United States Patent [19]

Ryan et al.

[11] Patent Number: 4,690,938

[45] Date of Patent: * Sep. 1, 1987

[54] ANTI-HYPERTENSIVE AGENTS

[75] Inventors: James W. Ryan; Alfred Chung, both of Miami, Fla.

[73] Assignee: University of Miami, Coral Gables, Fla.

[*] Notice: The portion of the term of this patent subsequent to Sep. 1, 2004 has been disclaimed.

[21] Appl. No.: 64,898

[22] Filed: Aug. 14, 1979

[51] Int. Cl.$^4$ .................... A61K 31/40; A61K 31/41; C07D 207/00; C07D 211/72

[52] U.S. Cl. .................... 514/362; 514/363; 514/423; 514/308; 514/255; 548/531; 548/535; 546/310

[58] Field of Search .................... 424/177, 301; 260/112.5; 548/531, 535; 546/310; 514/362, 363, 308, 255, 423

[56] References Cited

U.S. PATENT DOCUMENTS

| | | | |
|---|---|---|---|
| 3,832,337 | 8/1974 | Ondetti | 260/112.5 |
| 3,891,616 | 6/1975 | Ondetti | 260/112.5 |
| 3,947,575 | 3/1976 | Ondetti | 424/177 |
| 4,046,889 | 9/1977 | Ondetti | 424/319 X |
| 4,052,511 | 10/1977 | Cushman | 424/274 |
| 4,053,651 | 10/1977 | Ondetti | 424/319 X |
| 4,070,361 | 1/1978 | Petrillo | 260/293.85 |
| 4,091,024 | 5/1978 | Ondetti | 260/293.63 |
| 4,105,776 | 8/1978 | Ondetti | 424/274 |
| 4,105,789 | 8/1978 | Ondetti | 424/309 |
| 4,108,886 | 8/1978 | Ondetti | 260/455 R |
| 4,113,715 | 9/1978 | Ondetti | 424/274 |
| 4,116,962 | 9/1978 | Ondetti | 260/293.63 |
| 4,129,566 | 12/1978 | Ondetti | 546/326 |
| 4,146,611 | 3/1979 | Ondetti | 424/177 |
| 4,151,172 | 4/1979 | Ondetti | 260/326.2 |
| 4,154,840 | 5/1979 | Ondetti | 424/267 |
| 4,154,934 | 5/1979 | Bernstein | 546/189 |
| 4,154,935 | 5/1979 | Ondetti | 546/189 |
| 4,154,937 | 5/1979 | Cushman | 546/221 |
| 4,168,267 | 9/1979 | Petrillo | 260/326.2 |

OTHER PUBLICATIONS

Cushman et al., Biochemistry, vol. 16, 1977, p. 5484.
Cushman et al., Experientia, vol. 29, 1973, p. 1032.
Ondetti et al., Science, vol. 196, 1977, p. 441.
Dorer et al., Biochim. Biophys. Acta, vol. 429, 1976, p. 220.
Fisher et al., Arch. Biochem. Biophys., vol. 189, 1978, p. 81.
Gavras et al., N.E. J. Med., vol. 291, 1974, p. 817.
Gavras et al., N.E. J. Med., vol. 298, 1978, p. 991.
Lipmann, Accounts Chem. Res., vol. 6, 1973, p. 6.
Lehninger, Biochemistry, Worth Pub., N.Y., 1970, pp. 153–157.
Ryan et al., Tissue & Cell, vol. 10, 1978, p. 555.

Primary Examiner—Delbert R. Phillips

[57] ABSTRACT

Novel inhibitors of ACE are disclosed as potent inhibitors of angiotensin converting enzyme and as orally effective anti-hypertensive agents. The compounds have the general formula:

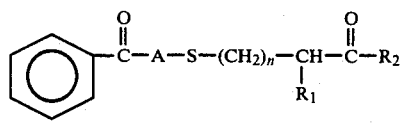

15 Claims, No Drawings

ANTI-HYPERTENSIVE AGENTS

BACKGROUND OF THE INVENTION

Angiotensin converting enzyme (peptidyldipeptide hydrolase, hereinafter referred to as ACE) occupies a central role in the physiology of hypertension. The enzyme is capable of converting the decapeptide angiotensin I, having the sequence

to an octapeptide, angiotensin II by removal of the carboxy-terminal HisLeu. The symbols for various chemical entities are explained in the following table:

| | |
|---|---|
| Ala = | L-alanine |
| Arg = | L-arginine |
| Asp = | L-aspartic acid |
| <Glu = | pyro-L-glutamic acid |
| Gly = | glycine |
| Hip = | Hippuric acid (Benzoyl glycine) |
| His = | L-histidine |
| Ile = | L-isoleucine |
| Leu = | L-leucine |
| Phe = | L-phenylalanine |
| Pro = | L-proline |
| ΔPro = | L-3,4-dehydroproline |
| Ser = | L-serine |
| Trp = | L-tryptophan |
| Tyr = | L-tyrosine |
| Val = | L-valine |
| ACE = | Angiotensin converting enzyme |
| Hepes = | N—2-hydroxyethylpiperazine-N'—2-ethanesulfonic acid |

Angiotensin I is formed by the action of the enzyme renin, an endopeptidase found in kidney, other tissues and plasma, acting on a serum α-2 globulin.

Blood pressure is affected by certain peptides found in the blood. One of these, angiotensin II, is a powerful pressor (blood pressure elevating) agent. Another, bradykinin, a nonapeptide with the sequence ArgProProGlyPheSerProPheArg is a powerful depressor (blood pressure lowering) agent. In addition to a direct pressor effect, angiotensin II stimulates release of aldosterone which tends to elevate blood pressure by causing retention of extracellular salt and fluids. Angiotensin II is found in measurable amount in the blood of normal humans. However, it is found at elevated concentrations in the blood of patients with renal hypertension.

The level of ACE activity is ordinarily in excess, in both normal and hypertensive humans, of the amount needed to maintain observed levels of angiotensin II. However, it has been found that significant blood pressure lowering is achieved in hypertensive patients by treatment with ACE inhibitors. [Gavras, I., et al., *New Engl. J. Med.* 291, 817 (1974)].

ACE is a peptidyldipeptide hydrolase. It catalyzes the hydrolysis of the penultimate peptide bond at the C-terminal end of a variety of acylated tripeptides and larger polypeptides having an unblocked α-carboxyl group. The action of ACE results in hydrolytic cleavage of the penultimate peptide bond from the carboxyl-terminal end yielding as reaction products a dipeptide and a remnant.

The reactivity of the enzyme varies markedly depending on the substrate. At least one type of peptide bond, having the nitrogen supplied by proline, is not hydrolyzed at all. The apparent Michaelis constant (Km) varies from substrate to substrate over several orders of magnitude. For general discussion of the kinetic parameters of enzyme catalyzed reactions, see Lehninger, A., Biochemistry, Worth Publishers, Inc., New York, 1970, pp. 153-157. Many peptides which are called inhibitors of the enzymatic conversion of angiotensin I to angiotensin II are in fact substrates having a lower Km than angiotensin I. Such peptides are more properly termed competitive substrates. Examples of competitive substrates include bradykinin, and the peptide BPP$_{5a}$ (also called SQ20475) from snake venom, whose sequence is <GluLysTrpAlaPro.

Numerous synthetic peptide derivatives have been shown to be ACE inhibitors by Ondetti, et al. in U.S. Pat. No. 3,832,337 issued Aug. 27, 1974.

The role of ACE in the pathogenesis of hypertension has prompted a search for inhibitors of the enzyme that could act as antihypertensive drugs. See for example U.S. Pat. Nos. 3,891,616, 3,947,575, 4,052,511 and 4,053,651. A highly effective inhibitor, with high biological activity when orally administered, is D-3-mercapto-2-methylpropanoyl-L-proline, designated SQ14225, disclosed in U.S. Pat. No. 4,046,889 to Ondetti et al., issued Sept. 6, 1977, and in scientific articles by Cushman, D. W. et al., *Biochemistry* 16, 5484 (1977), and by Ondetti, M. et al., Science 196, 441 (1977). The inhibitor SQ14225 reportedly has an I$_{50}$ value of $2.3 \times 10^{-8}$ M. The I$_{50}$ value reported by Cushman, et al, supra is the concentration of inhibitor required to produce 50% inhibition of the enzyme under a standard assay system containing substrate at a level substantially above K$_m$. It will be understood that I$_{50}$ values are directly comparable when all potential factors affecting the reaction are kept constant. These factors include the source of enzyme, its purity, the substrate used and its concentration, and the composition of the assay buffer. All I$_{50}$ data reported herein have been performed with the same assay system and same enzyme (human urinary ACE) and with an approximately ½ K$_m$ level of substrate and are therefore internally consistent. Discrepancies with data obtained by other workers may be observed. Indeed such discrepancies do exist in the literature, for unknown reasons. See, for example, the I$_{50}$ values for BPP$_{9a}$ reported by Cushman, D. W., et al., *Experientia* 29, 1032 (1973) and by Dorer, F. E., et al., *Biochim.Biophys.Acta* 429, 220 (1976).

The mode of action of SQ 14,225 has been based upon a model of the active site of ACE developed by analogy with the better known related enzyme, carboxypeptidase A. The active site was postulated to have a cationic site for binding the carboxyl end group of the substrate and a pocket or cleft capable of binding the side chain of the C-terminal amino acid and providing especially tight binding for the heterocyclic ring of a terminal proline residue. A similar pocket for the penultimate amino acid residue was postulated, and the published data suggested a rather stringent steric requirement, since the D-form of the inhibitor was substantially more potent than its stereoisomer or the 3-methyl and unsubstituted analogs. The sulfhydryl group on the inhibitor, postulated to be bound at the active site near the catalytic center, was believed to play a central role in inactivation of the enzyme by combining with the zinc moiety known to be essential for catalytic activity. Substituents on the sulfhydryl, such as a methyl group, and an S-acetyl derivative, substantially reduced potency of the inhibitor. See Cushman, D. W., et al., *Biochemistry*, supra.

In vitro study of the mechanism by which SQ 14,225 and its analogs act to inhibit ACE has been somewhat hampered by the instability of these molecules under ambient conditions. For example, it has been observed that a fresh aqueous solution of concentration, e.g., 1 mg per ml of SQ 14,225 at a pH of about 8 becomes substantially less active upon standing for as little as 30 minutes, and that activity continues to decrease as the solution stands for longer periods. It is believed that this loss in activity is mainly the result of dimerization of SQ 14,225 occurring at the sulfhydryl end groups, whereby a disulfide is formed which is largely inactive as an inhibitor. Since the free sulfhydryl group is highly reactive and may be readily oxidized to polar acidic moieties such as sulfone and sulfoxide groups, it may also be that the observed in vitro loss of activity of aqueous solutions of SQ 14,225 on standing is in some part a consequence of one or more such oxidation reactions, with formation of a sulfone or sulfoxide which does not function effectively as an inhibitor for ACE.

Such reports of SQ 14,225 clinical testing as are currently available, some of which refer to the compound under the name "Captopril", suggest that the product is sufficiently stable in the normal gastric and intestinal environments of most patients to be an effective inhibitor for ACE when administered orally. It is not yet clear, however, whether there may be a group of patients for which SQ 14,225 is substantially ineffective. Because of the high reactivity of the free sulfhydryl group, SQ 14,225 could readily form mixed disulfides with serum, cellular proteins, peptides or other free sulfhydryl group-containing substances in the gastric or intestinal environments, in addition to the possibility for dimer formation or oxidative degradation reactions. A mixed disulfide with protein may be antigenic and, indeed, occasional allergic reactions have been clinically observed. See Gavras, et al., *New England J. Med.* 298, 991 (1978). Disulfides and oxidative degradation products of SQ 14,225, if formed, may at best be expected to be largely ineffective as inhibitors. It may be postulated accordingly that dose response to SQ 14,225 may vary with conditions of administration and among individual patients. Moreover, in at least some patients, unwanted side effects may occur and maintenance of an effective concentration of the inhibitor in the body may be difficult to control.

Thiolester compounds generally are thought to be highly reactive in that the thiolester linkage is readily hydrolyzable to a sulfhydryl moiety and a carboxylic moiety. Thiolesters are accordingly often used as active ester intermediates for acylation under mild conditions. Such groups as, e.g., acetylthio have been used as blocking groups in the above cited Ondetti, et al. patents. Thiolester intermediates are also postulated to occur in the biosynthesis of cyclic peptides such as tyrocidin or gramicidin S. See Lipmann, F. in *Accounts Chem.Res.* 6, 361 (1973).

Thiolester compounds having potent ACE inhibitory activity and oral effectiveness as anti-hypertensive agents have been disclosed in copending applications Ser. No. 116,950, filed Jan. 30, 1980, which is a continuation of Ser. No. 941,289, filed Sept. 11, 1978 (now abandoned in favor of its pending continuation Ser. No. 116,950, filed Jan. 30, 1980) and Ser. No. 958,180, filed Nov. 6, 1978 (abandoned in favor of its continuation Ser. No. 116,951, filed Jan. 30, 1980 which was abandoned in favor of its continuation, Ser. No. 295, 589, filed Aug. 24, 1981 which was abandoned in favor of its continuation, Ser. No. 524,204, filed Aug. 18, 1983, which was abandoned in favor of its continuation, Ser. No. 680,541, filed Dec. 11, 1984, which was abandoned in favor of its pending continuation, Ser. No. 850,055, filed Apr. 10, 1986), both incorporated herein by reference. The previously disclosed compounds are: N-[3-(benzoylphenylalanylthio)-2-D-methylpropanoyl]-L-proline ($I_{50} \approx 1-4 \times 10^8$M), N-(2-benzoylphenylalanylthiopropanoyl)-L-proline ($I_{50} \approx 4-7 \times 10^{-8}$M for racemic compound), N-(3-benzoylphenylalanylthiopropanoyl)-L-proline ($I_{50} \approx 7 \times 10^{-7}$M), N-[3,4-(benzoylphenylalanylthio)-2-D-methylpropanoyl]-L-3,4dehydroproline, N-(2-benzoylphenylalanylthiopropanoyl)-L-3,4dehydroproline ($I_{50} = 3 \times 10^{-9}$M for racemic compound), and N-(3-benzoylphenylalanylthiopropanoyl)-L-3,4-dehydroproline. Unless noted otherwise, all amino acids are in their L-forms.

Compounds related to SQ 14,225 have been disclosed by Ondetti, et al., U.S. Pat. Nos. 4,046,889, 4,052,511, 4,053,651, 4,113,715 and 4,154,840. Of interest are disclosed analogs of SQ 14,225 having the five-membered heterocyclic ring of proline replaced by a four- or a six-membered ring. The inhibitory potencies of such analogs relative to SQ 14,225 are not disclosed. Substitution of D-proline for L-proline is reported to drastically reduce inhibitory potency of 3-mercaptopropanoyl amino acids (Cushman, D. W., et al., supra).

SUMMARY OF THE INVENTION

Novel inhibitors of ACE are disclosed which have the general formula

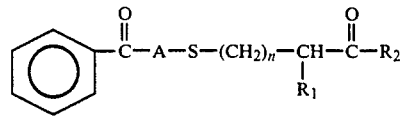

wherein,
A is glycyl, L-alanyl, L-leucyl, L-isoleucyl or L-valyl whose amino group is an amide linkage with the adjacent

$R_1$ is hydrogen or methyl;
$R_2$ is L-proline, L-3,4-dehydroproline, D,L-3,4-dehydroproline, L-3-hydroxyproline, L-4-hydroxyproline or L-thiazolidine-4-carboxylic acid whose imino group is an imide linkage with the adjacent

and
n is o or 1 such that when n=o, $R_1$ is methyl. The disclosed compounds are inhibitors of ACE and are useful as anti-hypertensive agents and are orally effective.

DETAILED DESCRIPTION OF THE INVENTION

The discovery of ACE inhibitory potency in the compounds of the present invention provides a unique approach to the design of inhibitory compounds. Although many prior art inhibitors are proline derivatives, substitution of other amino acids for proline has also yielded potent inhibitors. Arginine, phenylalanine and alanine are all effective substitutes for proline, so that a trend is not discernible.

The substitution of L-3,4-dehydroproline for proline has been studied in several systems. Substitution of L-3,4Δ Pro in the 7 position of bradykinin yields a bradykinin derivative which has significantly reduced physiological activity. See Fisher, G. H. et al., *Arch. Biochem. Biophys.* 189, 81 (1978). On the other hand, substitution of L-3,4- Δ Pro at the 3, 5 or 9 position in ACE inhibitor $BPP_{9a}$ enhances its inhibitory activity. In copending application Serial No. 958,180, applicants found that the compounds having Δ Pro, which are disclosed in said application, have high inhibitory potency and anti-hypertensive effectiveness. However, at present, no rationale can be advanced to explain the diversity of observed results following substitution of Δ Pro for proline. Similarly, no clear picture has emerged of the effects of other proline derivatives or analogs substituted at various loci on ACE inhibitors.

To date, the effect of the amino acid to the left of the sulfur in the above-shown formula, has not been determined. It is thought that this amino acid functions as an additional recognition site for the enzyme. If this is true, it would be expected that a compound with an amino acid here would be a better inhibitor. It was not known which, if any, amino acids would be effective in this position and which if any would enhance the inhibitory activity of a given compound. Applicants have found that various amino acids are effective and that the hydroxyprolines, proline, L-, and D,L-,3,4-dehydroproline, and thiazolidine-4-carboxylic acid derivatives are all effective anti-hypertensive agents and have high inhibitory potency for ACE.

The present invention will be further described by the following examples. In these examples, the thin-layer chromatography (TLC) was performed using silica gel plates. The numerical solvent systems for use in the TLC procedures are as follows.

(1) is methanol:chloroform, 1:1 (parts by volume). (2) is benzene:water:acetic acid, 9:1:9 (parts by volume). (3) is acetic acid:water:n-butanol 26:24:150 (parts by volume). (4) is n-butanol:pyridine:acetic acid:water, 15:10:3:12 (parts by volume). (5) is chloroform:methanol:ammonium hydroxide, 60:45:20 (parts by volume). The buffers for paper electrophoresis were: pH 1.9 -formic acid:acetic acid:water, 3:2:25 (parts by volume); pH 5.0 -diethylene glycol:acetic acid:pyridine:-water, 100:6:8.5:885 (parts by volume). The tert-butyloxycarbonyl derivatives of the amino acids are commercially available.

EXAMPLE 1

ACE activity assay

For most experiments described herein, the enzyme was assayed in 0.05M Hepes buffer, pH 8.0 containing 0.1M NaCl and 0.75M $Na_2SO_4$. The substrate employed was Benzoyl-GlyHisLeu at a final concentration of $1\times10^{-4}M$, ($K_m \approx 2\times10^{-4}M$), together with about 130,000 cpm of [$^3$H]-Benzoyl-GlyHisLeu (25 Ci/mmole). Enzyme was diluted in the above buffer such that 40 μl buffered enzyme was capable of hydrolyzing 13% of substrate in a 15-minute incubation at 37° C. To initiate the assay, 40 μl of enzyme and 10 μl of water or inhibitor dissolved in water were preincubated five minutes at 37° C. Substrate, 50 μl, was then added to initiate reaction and the solution was incubated for 15 minutes at 37° C. To terminate the reaction, 1 ml of 0.1M HCl was added, following which 1 ml of ethyl acetate was added. The mixture was agitated on a rotary mixer and centrifuged briefly to separate the phases.

An aliquot, 500 μl of the ethyl acetate layer was transferred to a liquid scintillation vial containing 10 ml of Riafluor, trademark New England Nuclear Corporation, Boston, Mass. For determination of $I_{50}$ values, enzyme activity in the presence of inhibitor at a series of different concentrations was compared to activity in the absence of inhibitor. A plot of inhibitor concentration versus percent inhibition yielded the $I_{50}$ value.

EXAMPLE 2

Synthesis of 3-acetylthiopropanoyl-L-proline-t-butyl ester 3-acetylthiopropanoic acid, 0.865 g, was dissolved in 2 ml redistilled tetrahydrofuran (THF) and cooled to 0° C. A cooled solution of dicyclohexylcarbodiimide, 1.2031 g in 2 ml of THF was added, following which a cooled solution of L-proline-t-butyl ester, 1 g, was added. The reaction mixture was stirred at 0° C. for one hour, then at 4° C. overnight. The reaction mixture was then filtered and the precipitate was washed with ethyl acetate. Solvents of the filtrates were removed under reduced pressure in a rotary evaporator. The residue was dissolved in ethyl acetate which was then washed three times with cold 1N citric acid, twice with saturated NaCl, twice with cold 1N $NaHCO_3$ and three times with saturated NaCl. The solution was dried over anhydrous $MgSO_4$ and filtered. The solvent was removed under reduced pressure in a rotary evaporator at 30° C. yielding a clear colorless oily product in approximately 87% yield. The product migrated as a single spot in thin layer chromatography in five solvent systems.

EXAMPLE 3

Synthesis of 3-mercaptopropanoyl-L-proline.

The product from Example 2, 3-acetylthiopropanoyl-L-proline-t-butyl ester, 0.5 g, was mixed with 4.5 ml of 5.5N methanolic ammonia at room temperature under nitrogen for one hour to remove the acetyl group. The solvent was then removed at 25° C. with a rotary evaporator. After the product was taken up in methanol and reevaporated twice more in the rotary evaporator, the clear oily residue was dissolved in ethyl ether, washed twice with 5% potassium bisulphate and once with saturated NaCl, dried over $MgSO_4$ and filtered. Residual solvent was removed in vacuo to yield a clear oily product, migrating as a single spot on thin layer chromatography in three separate solvent systems. The t-butyl ester protecting group was removed by reaction with trifluoroacetic acid in anisole.

EXAMPLES 4–6

By substituting 2-acetylthiopropanoic acid, 3-acetylthio-2-D-methylpropanoic acid, or 3-acetylthio-2-D,L-methylpropanoic acid for the 3-acetylthiopropanoic acid in Example 2 and substantially following the procedures of Examples 2 and 3, the following compounds are obtained. By removing the t-butyl ester protecting group with trifluoroacetic acid in anisole as a first step, the dicyclohexylamine salt can be formed to assist in the resolution of isomers. The acetyl protecting group can be removed in a second step using methanolic ammonia, as described in Example 3.

| Example | Compound |
|---|---|
| 4 | 2-mercaptopropanoyl-L-proline |
| 5 | 3-mercapto-2-D-methylpropanoyl-L-proline |
| 6 | 3-mercapto-2-D,L-methylpropanoyl-L-proline |

EXAMPLE 7

Synthesis of
3-mercapto-2-methyl-propanoyl-L-3,4-dehydroproline
L-3,4-dehydroproline L-3,4-dehydroproline ($\Delta^3$Pro), 1 mmole, is dissolved in DMF and the solution is cooled to $-15°$ C. The solution is neutralized by adding 1 equivalent of N-ethyl morpholine. In a separate reaction vessel at $-10°$ C., one equivalent of 3-acetylthio-2-methyl-propanoic acid in an equal volume of DMF is mixed with 1.1 equivalent of 1,1' carbonyldiimidazole, and the solution is stirred for one hour. The first solution containing $\Delta^3$Pro is mixed with the second, containing 3-acetylthio-2-methyl propanoic acid while maintaining the temperature at $-10°$ C. The combined solution is stirred for 1 hour at $-10°$ C. The solution is then allowed to warm slowly to room temperature. The solvent is removed on a rotary evaporator under reduced pressure at 40° C. Ethyl acetate (25 ml) is added and the solution is cooled to 0° C. Two ml of 1N citric acid is added, the two phases are mixed and then allowed to separate. The phases are separated with a separating funnel, and the organic phase is washed twice more with 2 ml 1N citric acid, two times with saturated NaCl and finally dried over anhydrous MgSO$_4$. The MgSO$_4$ is removed by filtration, and the solvent is removed with a rotary evaporator. The residue is dissolved and recrystallized from a non-polar solvent such as benzene to yield 3-acetylthio-2-D,L-methylpropanoyl-L-3,4-dehydroproline. When the 2-D-methyl isomer is desired, the residue is dissolved in acetonitrile (approximately 3 ml) and the solution is warmed to 40° C. One equivalent of dicyclohexylamine is added, and the solution is allowed to stand at room temperature overnight. The crystals are collected by filtration and are washed three times with acetonitrile. When further purification is required, the material can be recrystallized from isopropanol. The acetyl protecting group can be removed as in Example 3.

EXAMPLES 8-11

By substituting D,L-3,4-dehydroproline, L-3-hydroxyproline, L-4-hydroxyproline, or L-thiazolidine-4-carboxylic acid for the L-3,4-dehydroproline in Example 7 and substantially following the procedures of Example 7 the following compounds are obtained.

| Example | Compound |
|---|---|
| 8 | 3-mercapto-2-D-methylpropanoyl-D,L-3,4-dehydroproline |
| 9 | 3-mercapto-2-D-methylpropanoyl-L-3-hydroxyproline |
| 10 | 3-mercapto-2-D-methylpropanoyl-L-4-hydroxyproline |
| 11 | 3-mercapto-2-D-methyl-propanoyl-L-thiazolidine-4-carboxylic acid |

EXAMPLE 12

Similarly, by substituting 3-acetylthiopropanoic acid or 2-acetylthiopropanoic acid for the 3-acetylthio-2-methyl propanoic acid of Examples 7-11, the L-3,4-dehydroproline, D,L-3,4-dehydroproline, L-3-hydroxyproline, L-4-hydroxyproline and L-thiazolidine-4-carboxylic acid derivatives are obtained, following substantially the described procedures.

EXAMPLE 13

Synthesis of
N$^\alpha$-[3-(N$^\Delta$-benzoylglycylthio)-2-D-methylpropanoyl]-L-proline A solution of 33 mg of N$^\Delta$-benzoylglycine in 0.5 ml redistilled dimethylformamide (DMF) was cooled in an ice-dry ice-acetone bath at $-20°$ C. To this solution was added a cold solution of 35 mg of 1,1'-carbonyldiimidazole in 1.0 ml of DMF. The solution was stirred at $-10°$ C. for two hours and then mixed with a cold solution of 48 mg 3-mercapto-2-D-methylpropanoyl-L-proline in 1 ml of DMF which was neutralized with N-ethyl morpholine. The reaction mixture was stirred at $-10°$ C. for an additional hour and then slowly warmed to room temperature. The solvent was removed under reduced pressure at 40° C. and ethyl acetate was added to the residue. The mixture was cooled in an ice bath and washed with 0.1N HCl and then three times with saturated NaCl solution. The solvent was removed with a rotary evaporator after drying over anhydrous MgSO$_4$. The product was purified by liquid chromatography on Sephadex LH-2[1]/ using a 1.2 cm by 95 cm column and eluted with THF:isopropanol, 3:7 (parts by volume). The peak fractions were pooled and the solvent removed under reduced pressure yielding 37 mg of the named product. This product was found to be homogeneous using paper electrophoresis at pH 5.0 and using TLC with solvent systems 2, 3, 4 and 5.

[1]/ Trademark, Pharmacia, Inc., Uppsala, Sweden.

EXAMPLES 14-17

By substituting N$^\alpha$-benzoyl-L-alanine, N$^\alpha$benzoyl-L-isoleucine, N$^\alpha$-benzoyl-L-leucine, or N$^\alpha$-benzoyl-L-valine for the N$^\alpha$-benzoylglycine in Example 13 and substantially following the procedures of Example 13 the following compounds are obtained.

| Example | Compound |
|---|---|
| 14 | N$^\alpha$—[3-(N$^\alpha$—benzoyl-L-leucylthio)-2-D-methylpropanoyl]-L-proline |
| 15 | N$^\alpha$—[3-(N$^\alpha$ benzoyl-L-isoleucylthio)-2-D-methylpropanoyl]-L-proline |
| 16 | N$^\alpha$—[3-(N$^\alpha$—benzoyl-L-valylthio)-2-D-methylpropanoyl-L-proline |
| 17 | N$^\alpha$—[3-(N$^\alpha$—benzoyl-L-alanylthio)-2-D-methylpropanoyl]-L-proline |

EXAMPLE 18

Similarly, the L-3,4-dehydroproline, D,L-3,4-dehydroproline, L-3-hydroxyproline, L-4-hydroxyproline-4-carboxylic acid, and L-thiazolidine derivatives are obtained by substituting the products of Examples 3-12 for the 3-mercapto-2-D-methylpropanoyl-L-proline in Examples 13-17 and substantially following the procedures of Example 13.

EXAMPLE 19

The inhibitory potency of $N^\alpha$-[3-($N^\alpha$-benzoylglycylthio)-2-D-L-proline in vitro was measured in the assay described in Example 1. The enzyme preparation was ACE purified from human urine as described by Ryan, J. W., et al. *Tissue and Cell* 10,555 (1978). The $I_{50}$ was found to be $7.5 \times 10^{-9}$ M.

EXAMPLE 20

Oral effectiveness of
$N^\alpha$-[3-($N^\alpha$-benzoylglycylthio)-2-D-methyl-propanoyl]-L-proline Rats (210–290 g body weight) were fasted overnight and then anesthetized with intraperitoneal pentobarbital, 50–60 mg/kg. Tracheostomy was performed and the animals were ventilated mechanically. A cannula was inserted into a femoral vein for injection of angiotensin I, and a second cannula was inserted into a common carotid artery for direct measurement of arterial blood pressure. Heparin, 1,000 units, was injected via the femoral vein to prevent coagulation. Blood pressure was measured with a pressure transducer connected to a polygraph. The rats were injected with 400 ng/ml of angiotensin I in 20 μl of 0.9 g % NaCl; an amount of angiotensin I sufficient to raise mean arterial blood pressure by 38 mm Hg. After the responsiveness of a given rat to angiotensin I was established, the named compound at 20 μmol/kg (drug dissolved in 0.15 ml of H₂O plus 10 μl of 1N NaHCO₃), was given via a stomach tube. At timed intervals, the effects of 400 ng/kg of angiotensin I on mean arterial blood pressure were tested. Results are shown below:

| Time After Oral Administration (Minutes) | Blood Pressure Response to 400 ng/kg of Angiotensin I (% of Control) |
| --- | --- |
| −5 | 100 (38 mm Hg) |
| +1 | 95 |
| 6 | 95 |
| 11 | 95 |
| 22 | 92 |
| 28 | 68 |
| 33 | 61 |
| 39 | 58 |
| 45 | 47 |
| 60 | 47 |
| 67 | 45 |
| 74 | 47 |
| 82 | 47 |
| 92 | 47 |
| 137 | 55 |
| 142 | 55 |
| 152 | 47 |
| 185 | 63 |
| 207 | 79 |
| 230 | 74 |

EXAMPLE 21

Intravenous Effectiveness of
$N^\alpha$-[3-($N^\alpha$-benzoylglycylthio)-2-D-methylpropanoyl]-L-proline Anesthetized rats were prepared as described in Example 20. The animals were administered the named compound via a femoral vein in 15 μl of 0.01 N sodium bicarbonate, after the control response to 400 ng/kg of angiotensin I was measured. Intravenous administration of the named compound resulted in a rapid decrease of blood pressure response to angiotensin I, 400 ng/kg followed by a gradual rise to the pretreatment level of responsiveness. The time required for recovery of one-half of the lost responsiveness to angiotensin I, following injection of the named compound, was designated t1/2. For example, given the control response of 38 mmHg, an initial decrease of 19 mm would constitute a reduction to 50% of the control response, and t1/2 would be the time required for the mean arterial blood pressure response to angiotensin I to reach 28.5 mm (75% of control). Results are shown for two dose levels:

| Dose | t½ (minutes) |
| --- | --- |
| 0.23 μmol/kg | 26 |
| 0.7 μmol/kg | 36 |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A new compound having the formula

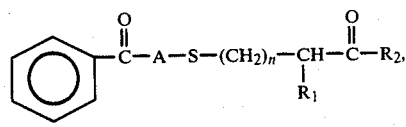

A is glycyl, L-isoleucyl, L-leucyl, or L-valyl whose amino group is in amide linkage with the adjacent

$R_1$ is hydrogen or methyl:
$R_2$ is a resdue of L-proline, L-3,4-dehydroproline, D,L-3,4-dehydroproline, L-3-hydroxyproline, L-4-hydroxyproline or L-thiazolidine-4-carboxylic acid whose imino group is in imide linkage with the adjacent

and, n is 0 or 1, such that when n=0, $R_1$ is methyl.

2. A compound of claim 1 wherein $R_2$ is L-proline.

3. A compound of claim 1 wherein $R_2$ is L-3,4-dehydroproline.

4. A compound of claim 1, 2 or 3 wherein A is glycyl, n is 1 and $R_1$ is methyl.

5. A compound of claim 1, 2 or 3 wherein A is L-alanyl, L-isoleucyl, L-leucyl or L-valyl.

6. A method for inhibiting angiotensin converting enzyme in vivo comprising administering an effective dose of a compound having the formula

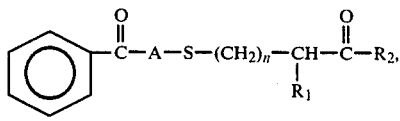

A is a residue of glycyl, L-alanyl, L-isoleucyl, L-leucyl, or L-valyl; whose amino group is in amide linkage with the adjacent

$R_1$ is hydrogen or methyl;

$R_2$ is L-proline, L-3,4-dehydroproline, D,L-3,4-dehydroproline, L-3-hydroxyproline, L-4-hydroxyproline or L-thiazolidine-4-carboxylic acid whose imino group is in imide linkage with the

and, n is 0 or 1, such that when n=0, $R_1$ is methyl.

7. The method of claim 6 wherein $R_2$ is L-proline.

8. The method of claim 6 wherein $R_2$ is L-3,4-dehydroproline.

9. The method of claim 6, 7 or 8 wherein A is glycyl, n is 1 and $R_1$ is methyl.

10. The method of 6, 7, or 8 wherein A is L-isoleucyl, L-alanyl, L-leucyl, or L-valyl.

11. A method for reducing blood pressure in vivo comprising administering an effective dose of a compound having the formula

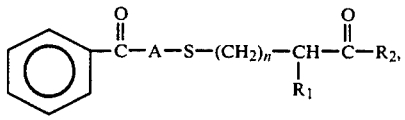

A is glycyl, L-alanyl, L-isoleucyl, L-leucyl, or L-valyl; whose amino group is a residue of in amide linkage with the adjacent

$R_1$ is hydrogen or methyl;

$R_2$ is L-proline, L-3,4-dehydropoline, D,L-3,4-dehydroproline, L-3-hydroxyproline, L-4-hydroxyproline or L-thiazolidine-4-carboxylic acid whose imino group is in imide linkage with the

and, n is 0 or 1, such that when n=0, $R_1$ is methyl.

12. The method of claim 11 wherein $R_2$ is L-proline.

13. The method of claim 11 wherein $R_2$ is L-3,4-dehydroproline.

14. The method of claims 11, 12, or 13 wherein A is glycyl, n is 1 and $R_1$ is methyl.

15. The method of claims 11, 12 or 13, wherein A is Lalanyl, L-isoleucyl, L-leucyl or L-valyl.

* * * * *

UNITED STATES PATENT AND TRADEMARK OFFICE
CERTIFICATE OF CORRECTION

PATENT NO. : 4,690,938
DATED : September 1, 1987
INVENTOR(S) : James W. Ryan and Alfred Chung It is certified that error appears in the above-identified patent and that said Letters Patent is hereby corrected as shown below:

Cover page - Col 1 - Insert the following omitted

U.S. Patent Documents:

| | | |
|---|---|---|
| 4,179,568 | 10/1978 | Cohen |
| 4,261,895 | 09/1978 | Wiskott |
| 4,283,407 | 09/1978 | Malen |
| 4,288,368 | 07/1979 | Haugwitz |
| 4,129,171 | 10/1977 | Ondetti |
| 3,865,934 | 4/1973 | Plotnikoff |
| 3,973,006 | 2/1975 | Ondetti |
| 3,976,770 | 2/1975 | Bumpus |
| 3,891,696 | 11/1973 | Bodor |
| 4,241,076 | 5/1979 | Ondetti et al. |
| 4,237,129 | 6/1979 | Ondetti et al. |

UNITED STATES PATENT AND TRADEMARK OFFICE
CERTIFICATE OF CORRECTION

PATENT NO. : 4,690,938

DATED : September 1, 1987

INVENTOR(S) : James W. Ryan and Alfred Chung

It is certified that error appears in the above-identified patent and that said Letters Patent is hereby corrected as shown below:

| | | |
|---|---|---|
| 4,237,134 | 6/1979 | Ondetti et al. |
| 4,234,489 | 6/1979 | Ondetti et al. |
| 4,217,359 | 8/1979 | Krapcho |
| 4,216,209 | 3/1979 | Bellini et al. |
| 4,211,786 | 3/1979 | Rovnyak |
| 4,206,137 | 11/1978 | Condon et al. |
| 4,206,122 | 4/1978 | Natarajan |
| 4,206,121 | 12/1978 | Ondetti et al. |
| 4,199,512 | 9/1978 | Ondetti et al. |
| 4,198,517 | 12/1978 | Ondetti |
| 4,198,515 | 12/1978 | Ondetti |
| 4,198,509 | 10/1978 | Losee et al. |
| 4,192,878 | 5/1978 | Ondetti |
| 4,186,268 | 1/1979 | Petrillo |
| 4,179,434 | 6/1978 | Ondetti et al. |
| 4,177,277 | 9/1978 | Ondetti et al. |
| 4,173,704 | 5/1978 | Ondetti et al. |
| 4,112,119 | 3/1977 | Ondetti et al. |
| 4,127,729 | 2/1978 | Ondetti |
| 4,128,721 | 2/1978 | Ondetti |

UNITED STATES PATENT AND TRADEMARK OFFICE
CERTIFICATE OF CORRECTION

PATENT NO. : 4,690,938

DATED : September 1, 1987

INVENTOR(S) : James W. Ryan and Alred Chung

It is certified that error appears in the above-identified patent and that said Letters Patent is hereby corrected as shown below:

| | | |
|---|---|---|
| 4,140,786 | 3/1978 | Ondetti et al. |
| 4,140,797 | 3/1978 | Ondetti et al. |
| 4,140,864 | 3/1978 | Ondetti et al. |
| 4,154,736 | 2/1978 | Ondetti et al. |
| 4,154,936 | 3/1978 | Ondetti et al. |
| 4,154,942 | 8/1978 | Ondetti et al. |
| 4,154,960 | 6/1978 | Ondetti et al. |
| 4,156,084 | 8/1978 | Ondetti et al. |
| 4,156,786 | 6/1978 | Ondetti et al. |
| 4,284,779 | 10/1977 | Ondetti et al. |
| 4,284,780 | 5/1978 | Ondetti et al. |
| 4,339,600 | 2/1978 | Ondetti et al. |
| 4,154,946 | 6/1978 | Ondetti et al. |
| 4,165,320 | 6/1978 | Ondetti et al. |
| 4,175,199 | 12/1978 | Ondetti et al. |
| 4,176,291 | 12/1978 | Ondetti et al. |
| 4,192,945 | 3/1979 | Ondetti |
| 4,220,791 | 3/1979 | Rovnyak |
| 4,225,495 | 12/1978 | Ondetti |

UNITED STATES PATENT AND TRADEMARK OFFICE
CERTIFICATE OF CORRECTION

PATENT NO. : 4,690,938
DATED : September 1, 1987
INVENTOR(S) : James W. Ryan and Alfred Chung It is certified that error appears in the above-identified patent and that said Letters Patent is hereby corrected as shown below:

4,235,885         6/1979         Sundeen et al.

Cover Page, Col 2 - Insert the following omitted

Foreign Patent Documents

| | | |
|---|---|---|
| 2457463 | 12/1974 | Fed. Rep. of Germany |
| 2703828 | 1/1977 | Fed. Rep. of Germany |
| 2407204 | 5/1979 | France |

Cover Page - Col 2 - Insert the following omitted reference:

Cronyn et al. J. Am. Chem. Soc., 74: 4726 (1952).
Fischer et al., Ber. 33:2383 (1900).
Fisher et al., FEBS Letters, 107:273 (1979).
Lehninger A., Biochemistry , pp. 189-194 (1975).
Ryan, J.W. et al., Biochem J., 167:501 (1977).
Methoden der Organischem Chem (Houben-Weyl), vol. XV, Pt. 1, p. 376 et seq., (1974).
Methoden der Organischem Chem (Houben-Weyl), vol, XV, Pt. II, p. 1 et seq., (1974).
Carter et al., J. Biol. Chem 138:627, (1941).
Engel et al., Proc. Soc. Exp. Biol. Med 143:483, (1973).

UNITED STATES PATENT AND TRADEMARK OFFICE
CERTIFICATE OF CORRECTION

PATENT NO. : 4,690,938

DATED : September 1, 1987

INVENTOR(S) : James W. Ryan and Alfred Chung

It is certified that error appears in the above-identified patent and that said Letters Patent is hereby corrected as shown below:

Jager et al., Chem. Ber. 103, 1727, (1970).

Klosterman et al., Biochem 6, 170. (1967).

Lijinski et al., Tetrahedron 26, 5137 (1970).

Nagasawa et al., J. Med. Chem. 16, 583, (1973).

Mita et al., Chem. Pharm. Bull. 26, (4), 1333-1335, (1978).

Kripalani et al., Clin, Pharmacol. Ther. 27 (5), 636-641, (1980).

Pfister et al., J. Am. Chem. Soc. 71 1096, (1949).

Merrifield, Avd Enzymol 32, 221, (1969).

Ricci et al., Anal Biochem. 79, 610, (1977).

Cushman, D.W. et al., Progr. Cardiovasc. Dis. 21, 176, (1978).

Oparil et al., Circ. Res 32, 415, (1973).

Oparil et al., Circ. Res 29, 682, (1971).

Dorer et al., Biochem. J. 141,915, (1974)

Sharpless, S.K., "Hypnotics and Sedatives", The Pharmacological Basis of Therapeutics, The Macmillian Co., (1965), pp. 105-128.

Kripalani, K.J. et al., Abstracts, Joint Meeting of ASPET/SOT, Aug. 13-17, 1978.

Singhvi, S.M. et al., Abstracts, Joint Meeting of ASPET/SOT, Aug. 13-17, 1978.

Wong, K.K. and Dreyfuss, J., Abstracts, Joint Meeting of ASPECT/SOT, Aug. 13-17, 1978.

UNITED STATES PATENT AND TRADEMARK OFFICE
CERTIFICATE OF CORRECTION

PATENT NO. : 4,690,938

DATED : September 1, 1987

INVENTOR(S) : James W. Ryan and Alfred Chung

It is certified that error appears in the above-identified patent and that said Letters Patent is hereby corrected as shown below:

Buxton et al., J. Chem. Soc., p. 366 (1954)

Col 4, line 11 delete "N-[3,4 ", and insert -- N-[3--

Col 8, line 11 delete "N$^\Delta$" to read --N$\big<$ --.

Col 8, line 15 delete "N$^\Delta$" to read --N$\big<$ --.

Col 8, line 33 delete "Sephadex LH-2" and insert
-- Sephadex LH-20--

Signed and Sealed this

Eighteenth Day of April, 1989

Attest:

DONALD J. QUIGG

Attesting Officer

Commissioner of Patents and Trademarks